(12) United States Patent
Boulanger

(10) Patent No.: US 11,964,107 B2
(45) Date of Patent: Apr. 23, 2024

(54) NITRIC OXIDE ADMINISTRATION IN HIGH FREQUENCY OSCILLATORY VENTILATION

(71) Applicant: L'Air Liquide, Société Anonyme pour l'Etude et l'Exploitation des Procédés Georges Claude, Paris (FR)

(72) Inventor: Thierry Boulanger, Philadelphia, PA (US)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 442 days.

(21) Appl. No.: 17/220,992

(22) Filed: Apr. 2, 2021

(65) Prior Publication Data

US 2021/0308411 A1 Oct. 7, 2021

Related U.S. Application Data

(60) Provisional application No. 63/004,157, filed on Apr. 2, 2020.

(51) Int. Cl.
*A61M 16/00* (2006.01)
*A61M 16/12* (2006.01)
*A61M 16/20* (2006.01)

(52) U.S. Cl.
CPC ........ *A61M 16/12* (2013.01); *A61M 16/0003* (2014.02); *A61M 16/20* (2013.01); *A61M 2016/0027* (2013.01); *A61M 2016/003* (2013.01); *A61M 2202/0275* (2013.01)

(58) Field of Classification Search
CPC .. A61M 16/12; A61M 16/0003; A61M 16/20; A61M 2202/0275; A61M 16/0858; A61M 16/024
See application file for complete search history.

(56) References Cited

U.S. PATENT DOCUMENTS

| 5,347,843 A * | 9/1994 | Orr | A61M 16/0858 600/538 |
| 5,379,650 A * | 1/1995 | Kofoed | G01F 1/50 73/861.75 |
| 5,558,083 A | 9/1996 | Bathe et al. | |
| 10,071,213 B2 | 9/2018 | Acker et al. | |
| 2004/0081580 A1 * | 4/2004 | Hole | A61K 33/00 604/23 |

(Continued)

FOREIGN PATENT DOCUMENTS

| EP | 3 372 267 | 9/2018 |
| WO | WO 2014 160373 | 10/2014 |
| WO | WO 2016 096056 | 6/2016 |

*Primary Examiner* — Margaret M Luarca
(74) *Attorney, Agent, or Firm* — Allen E. White

(57) ABSTRACT

The invention concerns a gas delivery system (1, 2) for providing gaseous Nitric Oxide (NO) to a patient comprising a medical ventilator (2) providing a respiratory gas, such as air, to a patient breathing circuit (3) having an inspiratory limb (31) with a flow sensor (100) and an NO injection module (110), and a NO-delivery device (1) for providing a NO-containing gas to the NO injection module (110) of the inspiratory limb (31), said NO delivery device (1) including a control unit (130) and a differential pressure sensor (104). The medical ventilator (2) can be a High Frequency Oscillatory (HFO) ventilator.

14 Claims, 2 Drawing Sheets

(56) References Cited

U.S. PATENT DOCUMENTS

| | | | |
|---|---|---|---|
| 2007/0034208 A1 | 2/2007 | Roehl et al. | |
| 2011/0023879 A1* | 2/2011 | Vandine | A61M 16/125 |
| | | | 128/204.21 |
| 2014/0275901 A1* | 9/2014 | Flanagan | A61B 5/7275 |
| | | | 600/364 |
| 2017/0043115 A1* | 2/2017 | Murphy | A61P 11/00 |
| 2017/0216551 A1* | 8/2017 | Acker | A61M 16/0069 |

* cited by examiner

NITRIC OXIDE ADMINISTRATION IN HIGH FREQUENCY OSCILLATORY VENTILATION

CROSS REFERENCE TO RELATED APPLICATIONS

This application claims the benefit of priority under 35 U.S.C. § 119 (a) and (b) to U.S. provisional patent application No. 63/004,157, filed Apr. 2, 2020, the entire contents of which are incorporated herein by reference.

BACKGROUND

The invention concerns a gas delivery system for providing gaseous NO to a patient comprising a medical ventilator, such as a HFO ventilator, providing a respiratory gas, such as air or the like, to a patient breathing circuit comprising a flow sensor and an injection module, and a NO delivery device for providing a NO-containing gas, such as a NO/$N_2$ mixture, to the injection module of the patient breathing circuit.

Nitric Oxide (hereafter NO) is a gas that, when inhaled, dilates the pulmonary blood vessels and increases oxygenation by improving gas exchanges in the lungs. These properties of NO are used for treating several medical conditions, such as Persistent Pulmonary Hypertension of the Newborn (PPHN) or Acute Respiratory Distress Syndrome (ARDS).

Usually, a low amount of gaseous NO (i.e. a few ppm vol.) diluted in nitrogen is mixed with an oxygen-containing gas and then inhaled by a patient in need thereof, according to a posology set by a physician. Typically, the $O_2$-containing gas is a $N_2/O_2$ mixture or air. In most cases, the NO concentration in the gas, after mixing, is between 2 and 80 ppm in volume (ppmv), depending on the treated population of patients, e.g. infants or adults.

The NO-containing gas inhaled by the patient is usually delivered by means of a NO delivery device usually connected to a mechanical ventilator as described by U.S. Pat. No. 5,558,083. The delivery device is fluidly connected to one or several gas cylinders containing a $N_2$/NO mixture containing between 200 and 800 ppmv of NO that provide said $N_2$/NO mixture to the NO delivery device. Generally, the NO delivery device further includes an injection module located in the inspiratory line of a breathing circuit fluidly connected to the mechanical ventilator and to a respiratory interface providing the NO-containing gas to a patient in need thereof.

The NO delivery device also includes a flow sensor which measures the flow delivered by the mechanical ventilator, such as air or a $N_2/O_2$ mixture, so as to compute and determine the right amount of NO to be delivered, based on the desired posology and taking into account the measured flowrate.

The NO delivery can be operated by means of a proportional solenoid valve associated to a flow sensor, both arranged into the delivery device, and a dedicated NO injection line, supplying the NO injection module as taught by U.S. Pat. No. 5,558,083. The delivery device continuously receives measurements of the gaseous flow, i.e. air or $N_2/O_2$, travelling into the inspiratory branch of the breathing circuit and adjusts, in real time the amount of NO to be delivered with respect to the set posology, by controlling the flow in the NO injection line based on the measurements from the internal flow sensor.

However, there are situations where such a configuration is problematic, in particular when the NO delivery system is associated with a high frequency oscillations (HFO) ventilator.

Indeed, HFO ventilators generate pressure oscillations of the gas at frequencies up to 20 Hz, wherein the pressure swings oscillate around a "mean pressure". Each oscillation is composed of a positive phase corresponding to a pressure greater than said "mean pressure", and a negative phase corresponding to a pressure lower than said "mean pressure". During the positive phase, the gas is delivered to the patient in tidal volumes, i.e. volumes as low as 0.5 mL, whereas the negative phase corresponds to the period of time during which the patient exhales.

In HFO ventilators, the amplitude of the pressure swings is very high. For example, a HFO jet ventilator can generate pressures as high as 1 bar relative during the positive phase. Such high amplitudes in pressure swings generate cyclic compressions/decompressions of the therapeutic gas in the injection line, which can be seen as false flow information by a separate NO therapeutic gas flow sensor in the injection line, and interpreted, for instance, as a reverse flow in the therapeutic gas injection line. For minimizing this phenomenon, processing of the flow information can be performed for instance as described by U.S. Pat. No. 10,071,213. The NO delivery device detects that the flow sensor measurements (for example) correspond to a HFO ventilator and a control system in the NO delivery device performs filtering, computation and/or interpolations on the flow measurement to take into account the compression/decompression phenomenon.

However, this contradicts the principle on which NO delivery devices are based, namely a proportional valve that relies on the accurate flow measurement of its internal flow sensor to ensure an accurate dose of NO.

In other words, if the method disclosed by U.S. Pat. No. 10,071,213 may improve the dosing accuracy, a perfect compensation is not possible due to the effect of filtering, computation and/or interpolations, and this data manipulation may also result in NO injection volume inaccuracies. Thus, although a NO delivery system based on a proportional valve and internal flow sensor can accurately dose the NO in cooperation with standard mechanical ventilation, it exhibits also limitations, when used with a HFO ventilator.

SUMMARY

A problem to be solved is therefore to provide an improved gas delivery system that does not encounter the above problems and drawbacks, in particular a gas delivery system for delivering accurate dose of NO to a patient, without the need of measurement data from any flow sensor arranged on the NO injection line.

A solution of the invention concerns a gas delivery system for providing gaseous NO to a patient comprising:
 a medical ventilator providing a respiratory gas to a patient breathing circuit comprising an inspiratory limb, said inspiratory limb comprising a breathing gas flow sensor and an NO injection module, and
 a NO delivery device for providing a NO-containing gas to the NO injection module of the inspiratory limb, said NO delivery device comprising a control unit and an inspiratory limb breathing gas flow sensor, said breathing gas flow sensor comprising a differential pressure sensor, characterized in that:
the breathing gas flow sensor cooperates with the differential pressure sensor for determining at least one differential pressure value and providing said at least one differential pressure value to the control unit, and
the control unit is configured for:
a) processing the at least one differential pressure value provided by the differential pressure sensor for determining an actual flow of respiratory gas in the inspiratory limb, and
b) using the actual flow of respiratory gas determined in step a) for determining an amount of NO-containing gas to be provided by the NO delivery device to the NO injection module, said NO injection module being configured for delivering said NO-containing gas in the inspiratory limb of the patient breathing circuit.

In the frame of the present invention, the terms:
The terms "breathing gas" and "respiratory gas" are used interchangeably herein.
"differential pressure value" are used for designating a numerical value of a differential pressure or a signal representative of a differential pressure that can be converted into a numerical value.
"NO-containing gas" are used for designating a gaseous mixture of NO with at least one additional gaseous component, typically an inert diluent gas, such as gaseous nitrogen.
"HFO-ventilator" are used for designating a medical respiratory apparatus or device delivering a respiratory gas using HFOV. A HFO ventilator delivers respiratory gas that is subjected to pressure oscillations at a high frequency, for instance up to 20 Hz.
"High Frequency Oscillatory Ventilation" or "HFOV" uses low tidal volumes and constant mean airway pressures in conjunction with high respiratory rates to provide beneficial effects on oxygenation and ventilation, while eliminating the traumatic "inflate-deflate" cycle imposed by conventional mechanical ventilation.

Depending on the embodiment, the gas delivery system can comprise one or several of the following features:
the breathing gas flow sensor is arranged in the inspiratory limb between the injection module and the medical ventilator.
the medical ventilator is a HFO-ventilator.
the breathing gas flow sensor comprises a flow restriction for creating a pressure differential (i.e. pressure drop) that is measured by the differential pressure sensor.
the injection module comprises at least one NO injection line comprising a solenoid valve controlled by the control unit.
the solenoid valve is an ON/OFF solenoid valve, i.e. a valve having 2 positions, i.e. one totally closed position (no gas can circulate) and one full open position (the total, maximum flow of gas can pass through it).
the at least one NO injection line further comprises a calibrated orifice arranged downstream of the solenoid valve.
the NO delivery device comprises several NO injection lines arranged in parallel, each NO injection line comprising a solenoid valve and preferably a calibrated orifice.
the NO delivery device further comprises a pressure regulator arranged upstream of the solenoid valve(s).
the NO injection module comprises a main NO injection conduit fluidly connected to several NO injection lines arranged in parallel for providing NO-gas to said several NO injection lines arranged in parallel, and a pressure regulator arranged in main NO injection conduit.
the inspiratory limb of the patient breathing circuit further comprises a gas humidifier, preferably arranged downstream of the NO injection module.
the breathing gas flow sensor comprises a flow restriction arranged between an upstream and a downstream chamber, i.e. inner compartment or the like, and the differential pressure sensor is fluidly connected to the upstream and downstream chambers of the flow sensor by an upstream and a downstream pressure line.
In addition to the differential pressure sensor, a breathing gas pressure sensor configured for measuring the breathing gas pressure upstream of the NO injection line(s) (that thus measures the incoming breathing gas pressure in the inspiratory limb) and providing breathing gas pressure measurement signals to the control unit, preferably a gage pressure sensor.
said pressure sensor is a gage pressure sensor.
the control unit is configured for compensating the effect of the incoming breathing gas pressure using the measurement of pressure provided by said breathing gas pressure sensor, especially a gage pressure sensor, for more accurately measuring the actual flow of breathing gas in the inspiratory limb, when the inspiratory limb is fluidly connected to a HFO-ventilator delivering pressure oscillations in the breathing gas circulating in said inspiratory limb.
the NO injection line does not comprise any flow sensor arranged between the solenoid valve and the NO injection module.
the control unit is configured for processing the at least one differential pressure value using a look-up table stored in a memory of the control unit, thereby determining the actual flow of respiratory gas in the inspiratory limb.
the control unit is configured for:
i) determining several successive actual flow values,
ii) calculating an average actual flow value using said successive actual flow values, and
iii) determining the amount of NO-containing gas provided to the NO injection module on the basis of said average actual flow values.
the amount of NO-containing gas is provided, i.e. delivered, by pulses by the NO delivery device to the NO injection module.
the amount of NO-containing gas is provided by pulses in controlling the opening and/or closing of the solenoid valve.
the pulse delivery is piloted by the control unit.
the control unit is configured for operating a time-pulse based delivery of NO-containing gas.
the control unit is configured for operating a time-pulse based delivery of NO-containing gas according to a duty cycle.
the medical ventilator provides a respiratory gas chosen among air and $N_2/O_2$ mixtures containing at least 21 vol. % of $O_2$.
the NO delivery device provides a NO-containing gas chosen among NO/nitrogen mixtures containing less than 1500 ppmv of NO, preferably less than 1000 ppmv of NO.
an electrical power source, such as batteries and/or the mains, provides electrical power (i.e. electric current), to the components of the NO delivery device in need thereof, such as the control unit, sensor . . . .

a NO-containing gas source is fluidly connected to the NO delivery device for providing a NO-containing gas, preferably a NO/$N_2$ mixture.

the NO-containing gas source comprises a gas cylinder.

the gas cylinder comprises a NO/$N_2$ mixture containing from about 200 to 800 ppmv of NO, the rest being $N_2$.

the patient breathing circuit further comprises an expiratory limb for recovering the gases expired by the patient, in particular the $CO_2$ enriched-gases expired by patient (P).

the inspiratory limb and the expiratory limb are fluidly connected to an Y-piece or the like.

the control unit comprises at least one microprocessor, preferably at least one microcontroller.

the control unit comprises at least one electronic board carrying said at least one microprocessor.

the at least one microprocessor runs one or several algorithms or the like.

the injection module comprises a housing.

at least a part of the NO injection line, the solenoid valve, the differential pressure sensor and the control unit are arranged in said housing.

the NO delivery device further comprises a pressure regulator for reducing the pressure of the NO-containing source gas.

the pressure regulator is arranged in said housing.

the differential pressure sensor is electrically connected to and/or outputs there from is processed by the control unit.

The invention deals also with a method for providing NO to a patient in need thereof, comprising using a gas delivery system for providing a gaseous mixture to the patient, said gaseous mixture comprising NO, $O_2$ and $N_2$.

Depending on the embodiment, the method can comprise one or several of the following features:

the patient can be an adult, a child, a baby or a neonate.

the gaseous mixture comprising NO, $O_2$ and $N_2$ contains less than 80 ppmv of NO, typically from about 2 to about 40 ppmv.

the patient is a neonate suffering from PPHN (i.e. Persistent Pulmonary Hypertension of the Newborn).

the ventilator is a HFO-ventilator.

the gaseous mixture comprising NO, $O_2$ and $N_2$ is obtained by injecting a NO/$N_2$ mixture into a flow of a respiratory gas of air or of a $O_2/N_2$ mixture containing at least 21 vol. % of $O_2$.

the gaseous mixture comprising NO, $O_2$ and $N_2$ is delivered to the patient by means of a respiratory interface, preferably a respiratory mask or tracheal intubation tube.

BRIEF DESCRIPTION OF THE DRAWINGS

The present invention will be explained in more details in the following illustrative description of an embodiment according to the present invention, which is made in references to the accompanying drawings among them.

DETAILED DESCRIPTION OF THE PREFERRED EMBODIMENTS

Figure 1:
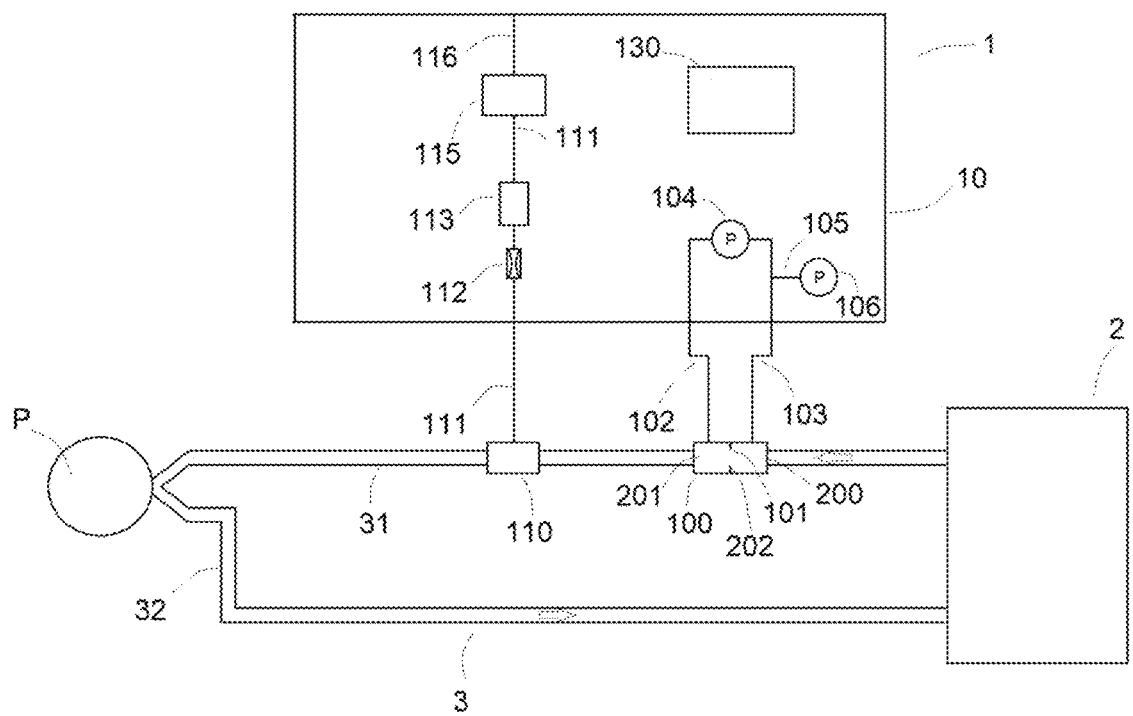
FIG. 1 illustrates an embodiment of gas delivery system for providing gaseous NO to a patient according to the present invention.

FIG. 1 shows an embodiment of a gas delivery system 1, 2 according to the present invention comprising a NO-delivery device 1 associated to a medical mechanical ventilator 2, i.e. a respiratory apparatus delivering a breathing gas, such as air or $N_2/O_2$ mixture, suitable for providing gaseous NO to a patient in need thereof.

The medical ventilator 2 provides a respiratory gas, such as air, to a breathing circuit 3 comprising gas conducts or the like, for conveying gas flows to the patient P in need thereof, i.e. for providing a ventilation assistance to the patient P.

More precisely, the breathing circuit 3 comprises an inspiratory limb 31 and an expiratory limb 32 that are coupled to a Y-piece of the like, that is in fluid communication with a respiratory interface for delivering gases to the patient P or recovering gases expired by said patient P, such as a respiratory mask, a tracheal intubation tube or the like.

Respiratory gases are travelling in the inspiratory limb 31 of the breathing circuit 3, from ventilator 2 toward the patient P, and are eventually inhaled by said patient P, whereas expiratory gases, i.e. $CO_2$ enriched-gases expired by patient P, are collected in the expiratory limb 32 of the breathing circuit 3, travel toward the mechanical ventilator 2 and are eventually vented to the atmosphere by the ventilator 2.

Further, a breathing gas flow sensor 100 and a NO injection module 110 are arranged in the inspiratory limb 31 of the breathing circuit 3. The breathing gas flow sensor 100 is preferably located/arranged in the inspiratory limb 31 between the NO injection module 110 and the ventilator 2.

The inspiratory limb 31 can also comprise a humidifier (not shown) for humidifying the respiratory gas before its delivering to the patient P, preferably the humidifier is located downstream of the NO injection module 110, between the NO injection module 110 and the patient P.

The breathing gas flow sensor 100 is used for measuring the gaseous flow, such as air, delivered by ventilator 2 that circulates in inspiratory limb 31, i.e. in its lumen. Preferably, breathing gas flow sensor 100 is a differential pressure-based flow sensor comprising an inner restriction 101 that creates a pressure differential, also called a pressure gradient or a pressure drop, in the gaseous flow circulating through said inner restriction 101. An upstream line 103 and a downstream line 102 are fluidly connected to the flow sensor 100, at sites located upstream and downstream of the inner restriction 101, for instance to an upstream 200 and a downstream 201 chamber of the breathing gas flow sensor 100 that are separated by an inner wall 202 comprising a gas passage forming the inner restriction 101.

The pressure difference created by the inner restriction 101 is measured by a differential pressure sensor 104 connected to the flow sensor 100, namely to the upstream 200 and downstream 201 chambers, by upstream and a downstream lines 102, 103, that constitute pressure measuring conducts or the like.

Preferably, the differential pressure sensor 104 is embedded in the housing 10 of the NO delivery device 1, and electrically connected (not shown) to and/or outputs there from are processed by a control unit 130, i.e. data processing system, computer or other electronic device, for instance a microprocessor arranged on an electronic board or the like. In other words, the control unit 130 processes the pressure signals or values delivered by the differential pressure sensor 104 that cooperates with flow sensor 100.

Of course, control unit 130 can also be configured to pilot any other electromechanical component embedded in the housing 10 of NO delivery device 1.

Control unit 130 stores a lookup table that allows a determination of the actual flow of respiratory gas flowing in the inspiratory limb 31 and flow sensor 100 thanks to a transformation of the pressure measured by the differential pressure sensor 104 into an actual breathing gas instantaneous flowrate value. Said actual flow rate of respiratory gas is afterwards used for determining an amount of NO to be added to the main flow of respiratory gas, such as air or an $O_2/N_2$ mixture, circulating in inspiratory limb 31 toward the patient P.

In other words, using the pressure measured by the differential pressure sensor 104 and a stored lookup table or the like, control unit 130 can determine the actual gas flow of respiratory gas (e.g. air) and an amount of NO to be added to it for obtaining a desired NO concentration in the mixture to be delivered to the patient P, typically a mixture containing $O_2$, $N_2$ and NO (generally <80 ppmv NO), thereby matching a set posology from a physician.

More precisely, based on the determination of the actual breathing gas flow in the inspiratory limb 31, control unit 130 determines the amount of NO, typically a mixture of NO and nitrogen, to be added by the NO injection module 110 to the respiratory gas travelling in inspiratory limb 31 to match the set posology.

Preferably, control unit 130 is configured for determining several successive actual flow values, calculating an average actual flow value using said successive actual flow values, and determining the amount of NO-containing gas to be provided to the injection module on the basis of said average actual flow value.

$NO/N_2$ mixture is fed by the NO delivery device 1 by NO injection line 111 providing NO to the NO injection module 110 arranged on the inspiratory limb 31.

The NO injection line 111 is fluidly connected to a high pressure (HP) line 116 having a high-pressure inlet that is fluidly connected to a NO source, typically a $NO/N_2$ cylinder (not shown) containing a pressurized gas (i.e. a $NO/N_2$ mixture) at a pressure of up to 200 bar abs or more. HP line 116 comprises a pressure regulator 115 that reduces the NO pressure to a low pressure (LP), such as a steady value of for instance about 4 bars abs. The low-pressure outlet of the pressure regulator 115 provides LP gas to the upper part of NO injection line 111 that further comprises a solenoid valve 113, preferably an ON/OFF solenoid valve 113, for controlling the flow of NO-containing gas in said NO injection line 111.

Preferably, said solenoid valve 113 can have a full-open or "ON" position, allowing a maximum NO-containing flow to travel in NO injection line 111 toward the injection module 110, and conversely a totally-close or "OFF" position, preventing any circulation of flow in NO injection line 111.

As shown in FIG. 1, pressure regulator 115, solenoid valve 113 and at least a part of NO injection line 111 and/or HP line 116 are arranged in housing 10 of the NO-delivery device 1.

A calibrated orifice 112 is further arranged in NO injection line 111, downstream of the ON/OFF solenoid valve 113 so as to define a fixed and predetermined flowrate of gas in the lumen of NO injection line 111, when the solenoid valve is on "ON", for instance a flowrate of about 0.1 L/min.

The $NO/N_2$ flow into NO injection line 111 is then injected into the main breathing gas flow provided by ventilator 2 that travels in inspiratory limb 31, such as an air or a $N_2/O_2$ mixture. Advantageously, the amount of NO-containing gas is provided in a pulse mode by the NO delivery device 1 to the NO injection module 110.

More precisely, the amount of NO-containing gas, i.e. the $NO/N_2$ mixture, is provided by pulses in controlling the opening or closing of the solenoid valve 113. This is done by the control unit 130 that pilots the solenoid valve.

For instance, the mechanical ventilator 2 can be operated for providing a steady flow of 1 L/min of air or of a $N_2/O_2$ mixture (with 21 vol. % $O_2$), and the delivery device 1 can be fluidly connected to a $NO/N_2$ cylinder containing 800 ppmv of NO.

In this case, control unit 130 determines that the instantaneous flow of NO gas travelling in injection line 111 should be of 0.025 L/min.

However, as the NO injection line 111 does not comprise any flow sensor arranged between the solenoid valve 113 and the injection module 110 for proportionally controlling the flow of NO gas, control unit 130 has to determine a 'duty cycle' repeated at fixed time intervals, typically time intervals of several tens of msec, namely a succession of gas delivery and interruption of gas delivery in the NO injection line 111, as explained below.

Figure 2:
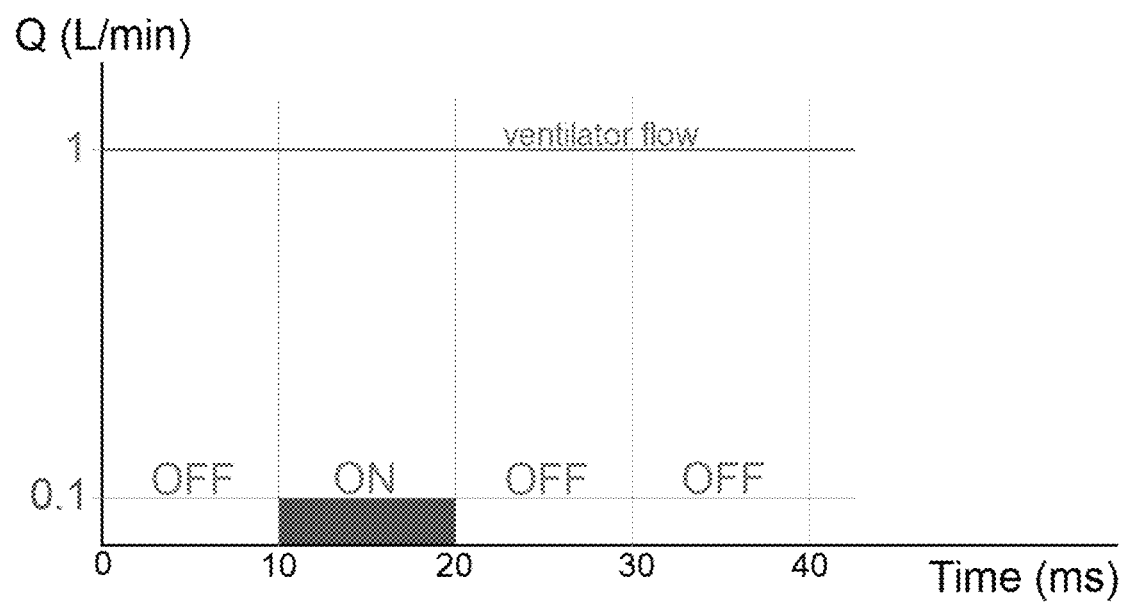
FIG. 2 shows a graph illustrating the dosing mechanism of the NO delivery device of FIG. 1 when delivering a continuous flow of NO.

FIG. 2 illustrates the delivery of NO gas according to the present invention during a time interval of 40 msec in a flow of air delivered by the mechanical ventilator 2 of 1 L/min.

In these conditions, a proportional delivery system according to the prior art should generate a continuous NO-flow of 0.025 L/min to meet a desired posology (e.g. 20 ppmv of NO), whereas the NO-delivery device 1 according to the present invention can only generate fixed flow amounts (i.e. discrete values) of NO in the NO injection line 111, e.g. 0.1 L/min.

The 'duty cycle' can be considered as a succession of gas delivery and end of gas delivery in the NO injection line 111 during a time interval, representing the ratio between continuous and discreet delivery.

In other words, instead of delivering a continuous flow (e.g. of 0.025 L/min) during the time interval (e.g. 40 msec in FIG. 2), control unit 130 pilots the NO delivery device 1, namely solenoid valve 113, for delivering about 0.1 L/min during only 25% of the considered time interval, i.e. during about 10 msec.

Control unit 130 controls solenoid valve 113 so that it is open during only 10 ms (25% of 40 msec) and closed during the rest of the time, i.e. during 30 msec.

Consequently, the volume measured by flow sensor 100 during a time interval of 40 ms would be 0.66 mL.

A continuous flow of 0.025 L/min during 40 ms would require the introduction of 0.016 mL of the NO containing gas into the NO injection line 111, which is equivalent, volume wise, to delivering a pulse of gas at 0.1 L/min for 10 ms or the 40 ms period.

As the flow spreading in inspiratory limb 31 is turbulent, homogenization of the NO concentration quickly occurs after its injection into said inspiratory limb 31.

Of course, control unit 130 can be configured for various time intervals, duration/frequency of the delivery or other parameters, depending on the desired conditions of use, such as the type of patient, the set posology, etc.

Generally speaking, according to the present invention, the operation of the ON/OFF solenoid valve 113 by control unit 130 defines a discrete or time pulsed NO-delivery device 1 that does not require any internal flowmeter to work.

Of course, several ON/OFF solenoid valves 113 and several calibrated orifices 112 may be arranged in parallel in order to generate different discrete pulses so that control unit 130 can determine, in real time, which combination of "ON and OFF" solenoids is the best, i.e. the more appropriate, at any given time interval, based on the breathing gas flow measured by flow sensor 100.

Furthermore, as already mentioned, medical ventilator 2 can be a HFO-type ventilator. HFO ventilators generate pressure oscillations of the respiratory gas at frequencies up to 20 Hz and significant amplitudes during the "positive" phases, e.g. inhalation phases of the patient, where volumes as low as 0.5 mL (or even less) can be inhaled by the patient, in particular when the patient is a small infant, a baby or a neonate.

Usually, HFO ventilators generate a baseline flow of air for instance, typically of between 2 and 15 L/min, that can be seen as a continuous flow, in the entire patient breathing circuit 3, namely in both the inspiratory 31 and the expiratory limb 32 of the patient breathing circuit 3. The baseline flow further "supports" additional flows generated during successive pressure swings that are inhaled by the patient P.

Considering a HFO ventilator set at 20 Hz, for which tidal volumes of 0.5 mL are generated and inhaled by patient P, the minute ventilation of a patient P is of about 0.6 mL/min, which corresponds to about 30% of a baseline flow set at 2 L/min.

However, accurate determination of the flow crossing breathing gas flow sensor 100 cannot be performed by differential pressure sensor 104 only, as the pressure applied in inspiratory limb 31 of breathing circuit 3 can vary greatly and reach up to 1 bar rel., in worst cases, for instance in high frequency jet ventilation.

Indeed, the flow/pressure relationship of differential pressure based flow sensors is a function of the density of the gas crossing the restriction 101 of flow sensor 100, and said density of the gas is linearly dependent to the pressure existing in the inspiratory limb 31. That is, the density of a gas at 2 bars abs. (i.e. 1 bar rel.) is twice the density of the same gas at ambient conditions, e.g. 1 bar abs. (at same temperature conditions, for instance 20° C.).

In order to take into account these variations, the NO delivery device also has a pressure sensor 106, ideally a gage pressure sensor, that measures, via a branch line 105, the pressure in the upstream line 103 that reflects the pressure in the inspiratory limb 31, as shown in FIG. 1.

By continuously receiving the measurement of pressure sensor 106, control unit 130 is able to compensate for the effect of pressure via a dedicated algorithm and accurately ascertain the actual flow of gas in inspiratory limb 31.

Figure 3:
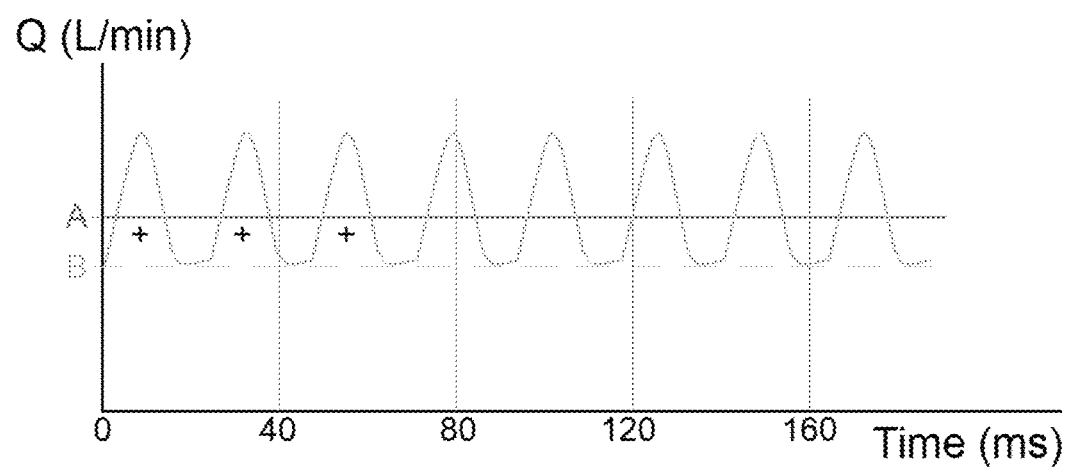
FIG. 3 illustrates the flow variations and the dosing mechanism of the gas delivery device coupled to a HFO-ventilator as shown in FIG. 1.

FIG. 3 illustrates a flow profile, processed by control unit 130, in HFO ventilation.

In this example, oscillations operated by the HFO ventilator 2 occur at a frequency of about 20 Hz, e.g. the positive phases (+) can last less than 20 ms (at 20 Hz, each oscillations has a duration of 50 msec, divided into inspiration and expiration), and are superimposed with a steady baseline flow B of air for instance.

The baseline flow (B) can be considered as a continuous component, whereas the fast oscillations can be seen as an alternate component whose frequency may be too high for the delivery device 1 to handle.

As control unit 130 is processing the signals of pressure and flow, the control unit 130 can easily detect the alternate, e.g. oscillating component, and determine that delivery device 1 is paired with a HFO-ventilator (i.e. mechanical ventilator 2) and undertake further signal processing in order to control solenoid valve 113 adequately.

For example, control unit 130 can determine the average value (A) of the flow spreading into inspiration limb 31 by using different filtration techniques, and actualize this average value (A), in order to define the interval period and duty cycle that will provide the NO dose set by the user, as shown in FIG. 2.

In other words, the control unit 130 is configured for determining several successive actual flow values, calculating an average actual flow value using said successive actual flow values, and determining the amount of NO-containing gas to be provided to the injection module 110 on the basis of said average actual flow value as said average actual flow value also reflects the use or not of a HFO ventilator.

According to the present invention, a time-pulse based gas delivery system 1 providing volume or boluses of NO containing gas into a breathing circuit 3 can be paired with any HFO ventilator 2 without requiring any internal flow sensor in the NO injection line 111, and further enhances the dosing accuracy.

According to the present invention, a time-pulse based gas delivery system 1 providing volume or boluses of NO containing gas into a breathing circuit 3 can be paired with any HFO ventilator 2 without requiring any internal flow sensor in the NO injection line 111, and further enhances the dosing accuracy.

What is claimed is:

1. A gas delivery system (1, 2) for providing gaseous Nitric Oxide (NO) to a patient comprising:
a medical ventilator (2) providing a respiratory gas to a patient breathing circuit (3) comprising an inspiratory limb (31), said inspiratory limb (31) comprising a respiratory gas flow sensor (100), said respiratory gas flow sensor (100) having a differential pressure sensor (104), and an NO injection module (110), and
a NO delivery device (1) for providing a NO-containing gas to the NO injection module (110) of the inspiratory limb (31), said NO delivery device (1) comprising a control unit (130), wherein:
the respiratory gas flow sensor (100) cooperates with the differential pressure sensor (104) for determining at least one differential pressure value and providing said at least one differential pressure value to the control unit (130), and
the control unit (130) is configured for:
a) processing the at least one differential pressure value provided by the differential pressure sensor (104) for determining an actual flow of respiratory gas in the inspiratory limb (31), and
b) using the actual flow of respiratory gas determined in step a) for determining an amount of NO-containing gas to be provided by the NO delivery device (1) to the NO injection module (110), said NO injection module (110) being configured for delivering said NO-containing gas in the inspiratory limb (31) of the patient breathing circuit (3),
wherein the NO injection module (110) comprises an NO injection line (111) comprising a solenoid valve (113) controlled by the control unit (130), and wherein the NO injection line (111) further comprises a calibrated orifice (112) arranged downstream of the solenoid valve (113).

2. The gas delivery system (1, 2) according to claim 1, wherein the respiratory gas flow sensor (100) is arranged in the inspiratory limb (31) between the NO injection module (110) and the medical ventilator (2).

3. The gas delivery system (1, 2) according to claim 1, wherein the medical ventilator (2) is a High Frequency Oscillatory (HFO)-ventilator.

4. The gas delivery system (1, 2) according to claim 1, wherein the respiratory gas flow sensor (100) comprises a flow restriction (101) for creating a pressure differential that is measured by the differential pressure sensor (104).

5. The gas delivery system (1, 2) according to claim 1, wherein the NO injection line (111) of the NO injection module (110) further comprises a pressure regulator (115) arranged upstream of the solenoid valve (113).

6. The gas delivery system (1, 2) according to claim 2, wherein the respiratory gas flow sensor (100) comprises a flow restriction (101) arranged between an upstream (200) and a downstream (201) chamber, and the differential pressure sensor (104) is fluidly connected to the upstream and downstream chambers (200, 201) of the respiratory gas flow sensor (100) by an upstream and a downstream pressure line (102, 103).

7. The gas delivery system (1, 2) according claim 1, wherein the NO injection module (110) further comprises a pressure sensor (106) configured for measuring the gas pressure in an inspiratory limb (31) upstream pressure line (103) and providing pressure measurement signals to the control unit (130).

8. The gas delivery system (1, 2) according claim 1, wherein the NO injection line (111) does not comprise any flow sensor arranged between the solenoid valve (113) and the NO injection module (110).

9. The gas delivery system (1, 2) according to claim 1, wherein the control unit (130) is configured for processing the at least one differential pressure value using a stored look-up table to thereby determine the actual flow of respiratory gas in the inspiratory limb (31).

10. The gas delivery system (1, 2) according to claim 1, wherein the control unit (130) is configured for:
    a) determining several successive actual flow values,
    b) calculating an average actual flow value using said successive actual flow values, and
    c) determining the amount of NO-containing gas to be provided to the NO injection module (110) on the basis of said average actual flow value.

11. The gas delivery system (1, 2) according to claim 1, wherein the amount of NO-containing gas is provided as pulses by the NO delivery device (1) to the NO injection module (110).

12. The gas delivery system (1, 2) according to claim 1, wherein the amount of NO-containing gas is provided as pulses by controlling the opening or closing of the solenoid valve (113).

13. The gas delivery system (1, 2) according to claim 1, wherein the medical ventilator (2) provides a respiratory gas chosen among air and $N_2/O_2$ mixtures containing at least 21 vol. % of $O_2$.

14. The gas delivery system (1, 2) according to claim 1, wherein the NO delivery device (1) provides a NO-containing gas chosen among NO/nitrogen mixtures containing less than 1000 ppmv of NO.

* * * * *